US011224263B2

(12) United States Patent
Darby et al.

(10) Patent No.: US 11,224,263 B2
(45) Date of Patent: Jan. 18, 2022

(54) MEDICAL SHOE HAVING A PLURALITY OF OUTSOLE PROJECTIONS

(71) Applicant: DARCO INTERNATIONAL, INC., Huntington, WV (US)

(72) Inventors: H. Darrel Darby, Mount Pleasant, SC (US); Wu Zhang, Proctorville, OH (US)

(73) Assignee: DARCO INTERNATIONA I;, INC., Huntington, WV (US)

( * ) Notice: Subject to any disclaimer, the term of this patent is extended or adjusted under 35 U.S.C. 154(b) by 0 days.

(21) Appl. No.: 15/559,623

(22) PCT Filed: Jun. 23, 2016

(86) PCT No.: PCT/US2016/038958
§ 371 (c)(1),
(2) Date: Sep. 19, 2017

(87) PCT Pub. No.: WO2017/222528
PCT Pub. Date: Dec. 28, 2017

(65) Prior Publication Data
US 2019/0116924 A1     Apr. 25, 2019

(51) Int. Cl.
*A61F 5/01*     (2006.01)
*A43B 7/32*     (2006.01)
(Continued)

(52) U.S. Cl.
CPC .................. *A43B 7/32* (2013.01); *A43B 3/12* (2013.01); *A43B 3/128* (2013.01); *A43B 3/24* (2013.01);
(Continued)

(58) Field of Classification Search
CPC ........... A43B 7/32; A43B 3/128; A43B 3/244; A43B 13/223; A61F 5/0195
See application file for complete search history.

(56) References Cited

U.S. PATENT DOCUMENTS 3,538,628 A   11/1970   Einstein, Jr.
3,902,259 A    9/1975   Cracco
(Continued)

FOREIGN PATENT DOCUMENTS

| KR | 200468794 Y1 | 9/2013 |
| TW | 201607523 A | 3/2016 |
| WO | 2016/014828 A1 | 1/2016 |

OTHER PUBLICATIONS

International Search Report of PCT/US2016/038958 dated Oct. 28, 2016 [PCT/ISA/210].
(Continued)

*Primary Examiner* — Jila M Mohandesi
(74) *Attorney, Agent, or Firm* — Sughrue Mion, PLLC

(57) ABSTRACT

A medical shoe having a plurality of outsole projections is provided. The medical shoe may include a sole assembly configured to support a foot, and a frame surrounding the sole assembly. The sole assembly may include a midsole portion forming a substantially planar surface for supporting the foot and an outsole portion including the plurality of outsole projections extending from the midsole portion. The frame may include a plurality of through holes corresponding to the plurality of outsole projections. The plurality of outsole projections may extend through the plurality of through holes so as to form a ground contacting surface. The plurality of outsole projections may also be provided in a symmetrical pattern. The sole assembly may be secured to the frame by a self-locking fit between the sole assembly and the frame.

21 Claims, 13 Drawing Sheets

(51) Int. Cl.
| | |
|---|---|
| A43B 13/18 | (2006.01) |
| A43B 3/24 | (2006.01) |
| A43B 7/14 | (2006.01) |
| A43B 7/20 | (2006.01) |
| A43B 11/00 | (2006.01) |
| A43B 13/04 | (2006.01) |
| A43B 23/08 | (2006.01) |
| A43B 17/00 | (2006.01) |
| A43C 11/14 | (2006.01) |
| A43B 13/14 | (2006.01) |
| A43B 7/08 | (2006.01) |
| A43B 19/00 | (2006.01) |
| A43B 13/22 | (2006.01) |
| A43B 3/12 | (2006.01) |
| A43B 13/26 | (2006.01) |
| A43B 13/12 | (2006.01) |
| A43B 13/36 | (2006.01) |
| A43B 1/00 | (2006.01) |
| A43C 11/06 | (2006.01) |

(52) U.S. Cl.
CPC ............... *A43B 3/244* (2013.01); *A43B 7/08* (2013.01); *A43B 7/14* (2013.01); *A43B 7/1405* (2013.01); *A43B 7/1415* (2013.01); *A43B 7/20* (2013.01); *A43B 11/00* (2013.01); *A43B 13/04* (2013.01); *A43B 13/122* (2013.01); *A43B 13/14* (2013.01); *A43B 13/184* (2013.01); *A43B 13/188* (2013.01); *A43B 13/22* (2013.01); *A43B 13/223* (2013.01); *A43B 13/26* (2013.01); *A43B 13/36* (2013.01); *A43B 17/00* (2013.01); *A43B 19/00* (2013.01); *A43B 23/086* (2013.01); *A43B 23/087* (2013.01); *A43C 11/14* (2013.01); *A61F 5/0195* (2013.01); *A43B 1/0054* (2013.01); *A43B 7/085* (2013.01); *A43C 11/06* (2013.01); *A43C 11/1493* (2013.01)

(56) References Cited

U.S. PATENT DOCUMENTS

| | | | |
|---|---|---|---|
| 4,179,826 A | 12/1979 | Davidson | |
| 4,255,874 A | 3/1981 | Sironi | |
| 4,267,650 A * | 5/1981 | Bauer | A43B 13/36 36/101 |
| 4,314,412 A | 2/1982 | Anderson et al. | |
| 4,372,059 A | 2/1983 | Ambrose | |
| 4,377,042 A * | 3/1983 | Bauer | A43B 13/36 36/101 |
| 4,564,966 A | 1/1986 | Chen | |
| 4,654,983 A | 4/1987 | Graham et al. | |
| 4,656,760 A | 4/1987 | Tonkel et al. | |
| 5,014,449 A | 5/1991 | Richard et al. | |
| 5,067,256 A | 11/1991 | Darby | |
| 5,083,385 A * | 1/1992 | Halford | A43B 13/36 36/100 |
| 5,317,822 A * | 6/1994 | Johnson | A43B 13/36 36/101 |
| 5,329,705 A | 7/1994 | Grim et al. | |
| 5,367,791 A * | 11/1994 | Gross | A43B 13/181 36/25 R |
| 5,464,385 A * | 11/1995 | Grim | A61F 5/0127 602/23 |
| 5,642,575 A | 7/1997 | Norton et al. | |
| 5,775,005 A | 7/1998 | McClelland | |
| 5,799,417 A * | 9/1998 | Burke | A43B 3/0047 36/105 |
| 5,961,477 A * | 10/1999 | Turtzo | A61F 5/0111 602/12 |
| 6,038,790 A | 3/2000 | Pyle et al. | |
| 6,345,454 B1 * | 2/2002 | Cotton | A43B 3/24 36/101 |
| 6,915,596 B2 * | 7/2005 | Grove | A43B 13/223 36/100 |
| 6,931,766 B2 * | 8/2005 | Greene | A43B 3/122 36/100 |
| 7,140,129 B2 * | 11/2006 | Newson | A43B 5/18 36/100 |
| 7,418,755 B2 * | 9/2008 | Bledsoe | A43B 7/28 12/142 N |
| 7,793,429 B2 | 9/2010 | Ellis, III | |
| 7,946,059 B2 | 5/2011 | Borel | |
| 7,966,748 B2 | 6/2011 | Votolato | |
| 8,020,318 B2 | 9/2011 | Khalifa | |
| 8,225,532 B2 | 7/2012 | Chen | |
| 8,291,619 B2 | 10/2012 | Abadjian | |
| 8,323,282 B2 * | 12/2012 | Taylor | A61B 17/62 606/59 |
| 8,474,155 B2 | 7/2013 | Mcdonald et al. | |
| 9,510,965 B2 * | 12/2016 | Grim | A61F 5/0111 |
| 9,744,065 B2 * | 8/2017 | Walborn | A61F 5/0102 |
| 2002/0050079 A1 | 5/2002 | Yoshiaki | |
| 2002/0073578 A1 | 6/2002 | Ellis, III | |
| 2003/0046832 A1 | 3/2003 | Knoerr et al. | |
| 2003/0196353 A1 | 10/2003 | Baek | |
| 2004/0194351 A1 | 10/2004 | Gallegos | |
| 2004/0255486 A1 | 12/2004 | Pawlus et al. | |
| 2005/0188562 A1 | 9/2005 | Clarke et al. | |
| 2005/0268490 A1 | 12/2005 | Foxen | |
| 2006/0137221 A1 * | 6/2006 | Dojan | A43B 13/20 36/29 |
| 2007/0017124 A1 | 1/2007 | Koo et al. | |
| 2007/0186446 A1 | 8/2007 | Lafortune | |
| 2007/0240338 A1 | 10/2007 | Din Mahamed | |
| 2007/0245504 A1 | 10/2007 | Spector | |
| 2008/0000108 A1 | 1/2008 | Ellis, III | |
| 2008/0047167 A1 | 2/2008 | Pawlus et al. | |
| 2008/0141565 A1 * | 6/2008 | Rini | A43B 23/087 36/77 R |
| 2009/0071041 A1 | 3/2009 | Hooper | |
| 2009/0126230 A1 | 5/2009 | McDonald et al. | |
| 2009/0320329 A1 | 12/2009 | Darby, II et al. | |
| 2010/0146819 A1 | 6/2010 | Teteriatnikov et al. | |
| 2010/0170114 A1 | 7/2010 | Jara et al. | |
| 2010/0275471 A1 | 11/2010 | Teteriatnikov et al. | |
| 2010/0324461 A1 | 12/2010 | Darby, II et al. | |
| 2011/0283560 A1 | 11/2011 | Portzline et al. | |
| 2012/0073160 A1 | 3/2012 | Marvin et al. | |
| 2012/0180344 A1 | 7/2012 | Crowley, II et al. | |
| 2012/0317845 A1 | 12/2012 | Vattes | |
| 2013/0160331 A1 | 6/2013 | Burke et al. | |
| 2013/0269213 A1 | 10/2013 | Gift et al. | |
| 2015/0181976 A1 | 7/2015 | Cooper et al. | |
| 2016/0045354 A1 | 2/2016 | Lee et al. | |
| 2019/0116925 A1 | 4/2019 | Darby et al. | |

OTHER PUBLICATIONS

Written Opinion of PCT/US2016/038958 dated Oct. 28, 2016 [PCT/ISA/237].
Communication dated Jun. 19, 2019, from the European patent Office in application No. 16906451.6.
Communication dated Jul. 9, 2019, from the European Patent Office in application No. 16906451.6.
International Search Report dated Sep. 14, 2016, in application No. PCT/US2016/038949.
Written Opinion of the International Searching Authority dated Sep. 14, 2016, in application No. PCT/US2016/038949.
Communication dated Apr. 10, 2019 from the United States Patent and Trademark Office in U.S. Appl. No. 15/559,656.
Communication dated Jul. 29, 2019 from the United States Patent and Trademark Office in U.S. Appl. No. 15/559,656.
U.S. Appl. No. 15/559,656, Pending.

(56) References Cited

OTHER PUBLICATIONS

Communication dated Jun. 23, 2020, from The China National Intellectual Property Administration in Application No. 201680086221.2.

* cited by examiner

MEDICAL SHOE HAVING A PLURALITY OF OUTSOLE PROJECTIONS

BACKGROUND

1. Field

Apparatuses and methods consistent with the present disclosure relate to a medical shoe for supporting a post-operative or otherwise traumatized patient's foot, and more particularly to a surgical shoe having a plurality of outsole projections configured to provide a customized weight distribution across a patient's foot. For example, the outsole projections may be configured to offload pressure at a location of a wound or other traumatized area of the patient's foot.

2. Description of the Related Art

Medical shoes play an essential role in recovery following surgery or other trauma to a patient's foot. For instance, the medical shoe may assist in redistributing weight away from the wound or traumatized area, such that the wound or traumatized area may heal.

However, such medical shoes may be prohibitively expensive, as they often require labor intensive manufacturing steps including gluing and stitching. Additionally, these manufacturing steps are often susceptible to failure, and frequently result in shortening the usable life of the medical shoe.

As a result, there are no suitable post-trauma medical shoes that effectively redistribute weight away from a wound or traumatized area of a patient's foot without requiring labor intensive manufacturing methods including gluing and stitching to assemble the medical shoe.

There is therefore a need to provide a post-trauma medical shoe that does not require labor intensive and failure prone manufacturing methods including gluing and/or stitching (or minimizes the same), designed to be used by patients who have experienced either surgery of the foot, trauma to the foot, or have foot pain aggravated by weight bearing such as heel spur syndrome, plantar fasciitis, calcinosis, Achilles tendonitis, or have skin lesions, ulcers or infections of the foot area where reduction of weight would enhance the healing process and allow the patient to be ambulatory.

SUMMARY

According to one aspect of an exemplary embodiment, a medical shoe includes a sole assembly configured to support a foot, the sole assembly including: a midsole portion forming a substantially planar surface for supporting the foot; and an outsole portion comprising a plurality of outsole projections extending from the midsole portion; and a frame surrounding the sole assembly, the frame including a plurality of through holes corresponding to the plurality of outsole projections. The plurality of outsole projections may extend through the plurality of through holes in the frame so as to form a ground contacting surface. The plurality of outsole projections may be provided in a symmetrical pattern. The sole assembly may be secured to the frame by a self-locking fit between the sole assembly and the frame.

The sole assembly may further include a sole assembly lip portion extending around a circumferential edge of the sole assembly in a direction perpendicular to the substantially planar surface. The frame may further include a frame lip portion surrounding the sole assembly lip portion such that a contour of an inner surface the frame lip portion corresponds to a contour of an outer surface the sole assembly lip portion. The self-locking fit may include a frictional force between the sole assembly and the frame.

The sole assembly may further include a fixation projection extending from the sole assembly lip portion in a direction parallel to the substantially planar surface. The frame may further include a fixation projection through hole in the frame lip portion. The fixation projection may extend into the fixation projection through hole.

The midsole portion may include a rear heel portion, a midfoot portion, and a front forefoot portion; and the plurality of outsole projections may include: a plurality of outsole forefoot projections extending from the front forefoot portion; a plurality of outsole midfoot projections extending from the midfoot portion, and an outsole heel projection extending from the rear heel portion.

A thickness of at least one of the plurality of outsole midfoot projections may be greater than a thickness of the outsole heel projection. A thickness of at least one of the plurality of outsole midfoot projections may be greater than a thickness of at least one of the plurality of outsole forefoot projections.

The sole assembly may be composed of ethylene-vinyl acetate. The plurality of outsole projections may have a non-uniform density.

The medical shoe may further include a removable cover secured to the frame and located above the sole assembly, such that a cavity configured to surround the foot is defined by a bottom surface of the removable cover and a top surface of the sole assembly. The removable cover may include ventilation holes.

The medical shoe may further include a fixation element and a closure strap. The fixation element may be secured to a fixation projection extending from the frame. The fixation element may include a fixation element slot configured to receive the closure strap. The removable cover may include a removable cover slot configured to receive the closure strap. The closure strap may be positioned through the fixation element slot and through the removable cover slot.

The medical shoe may further include a removable insole located on the substantially planar surface. The removable insole may include a foot supporting portion; and a plurality of pressure distribution pegs extending from the food supporting portion towards the substantially planar surface. The plurality of pressure distribution pegs may be non-uniform in height.

According to an aspect of an exemplary embodiment, a snap fit medical shoe assembly includes a sole assembly configured to support a foot, the sole assembly including: a midsole portion forming a substantially planar surface for supporting the foot; an outsole portion comprising a plurality of outsole projections extending from the midsole portion; and a sole assembly lip portion extending around a circumferential edge of the sole assembly in a direction perpendicular to the substantially planar surface; a rigid exoskeleton configured to surround the sole assembly, the rigid exoskeleton including a plurality of through holes corresponding to the plurality of outsole projections and an exoskeleton lip portion corresponding to the sole assembly lip portion; and a removable cover configured to be secured to the rigid exoskeleton. The plurality of outsole projections may be configured to extend through the plurality of through holes in the rigid exoskeleton so as to form a ground contacting surface. A contour of an inner surface the exoskeleton lip portion may correspond to a contour of an outer surface the sole assembly lip portion, such that the sole assembly is configured to be secured to the rigid exoskeleton by a snap fit between the sole assembly and the rigid exoskeleton.

The midsole portion may include a rear heel portion, a midfoot portion, and a front forefoot portion. The plurality of outsole projections may include a pair of outsole midfoot projections extending from the midfoot portion, and only one of: an outsole heel projection extending from the rear heel portion; or a pair of outsole forefoot projections extending from the front forefoot portion. The plurality of outsole projections may be provided in a symmetrical pattern.

The plurality of outsole projections may include the pair of outsole forefoot projections extending from the front forefoot portion. The pair of outsole forefoot projections may be provided at an angle with respect to the substantially planar surface.

The plurality of outsole projections may include a total of 7 outsole projections.

According to an aspect of an exemplary embodiment, a method of attaching orthopedic bracing includes: providing a sole assembly configured to support a foot of a patient, the sole assembly including: a midsole portion forming a substantially planar surface for supporting the foot; and an outsole portion comprising a plurality of outsole projections extending from the midsole portion; providing a rigid exoskeleton, the rigid exoskeleton including a plurality of through holes corresponding to the plurality of outsole projections; positioning the sole assembly into an interior of the rigid exoskeleton such that the plurality of outsole projections extend through the plurality of through holes in the rigid exoskeleton, the plurality of outsole projections forming a ground contacting surface, such that the sole assembly is secured to the rigid exoskeleton by a snap fit between the sole assembly and the rigid exoskeleton; positioning the substantially planar surface adjacent to a bottom portion of the foot of the patient; and positioning a removable cover adjacent to a top portion of the foot of the patient and securing the removable cover to the rigid exoskeleton. The plurality of outsole projections may be provided in a symmetrical pattern.

The providing the sole assembly may include providing a sole assembly based on data of the foot of the patient, such that the plurality of outsole projections are oriented according to a medical condition of the patient.

The providing the rigid exoskeleton may include providing a rigid exoskeleton not based on the data of the foot of the patient.

The medical condition of the patient may be one from among: surgery of the foot, trauma of the foot, a wound of the foot, and an ulceration of the foot.

BRIEF DESCRIPTION OF THE DRAWINGS

These and/or other aspects will become apparent and more readily appreciated from the following description of the exemplary embodiments, taken in conjunction with the accompanying drawings, in which.

DETAILED DESCRIPTION

Merits and features of the present disclosure, and a method for accomplishing the merits and features, will become apparent upon reference to the exemplary embodiments described below with the accompanying drawings. However, the present disclosure may be embodied in many different forms and should not be construed as being limited to the embodiments set forth herein. Rather, these embodiments are provided so that this disclosure will be thorough and complete, and will fully convey the concept of the disclosure to those of ordinary skill in the art. The scope of the disclosure is defined only by the claims.

Figure 1:
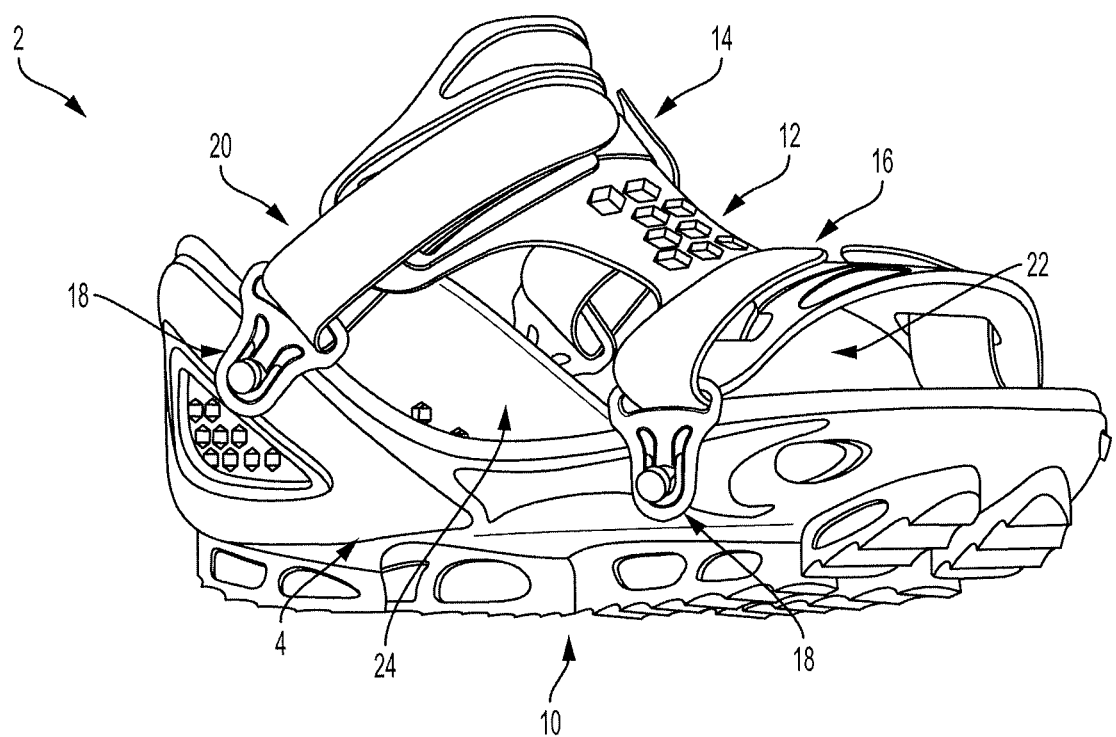
FIG. 1 is a side view of a medical shoe according to an aspect of an exemplary embodiment.
Figure 2:
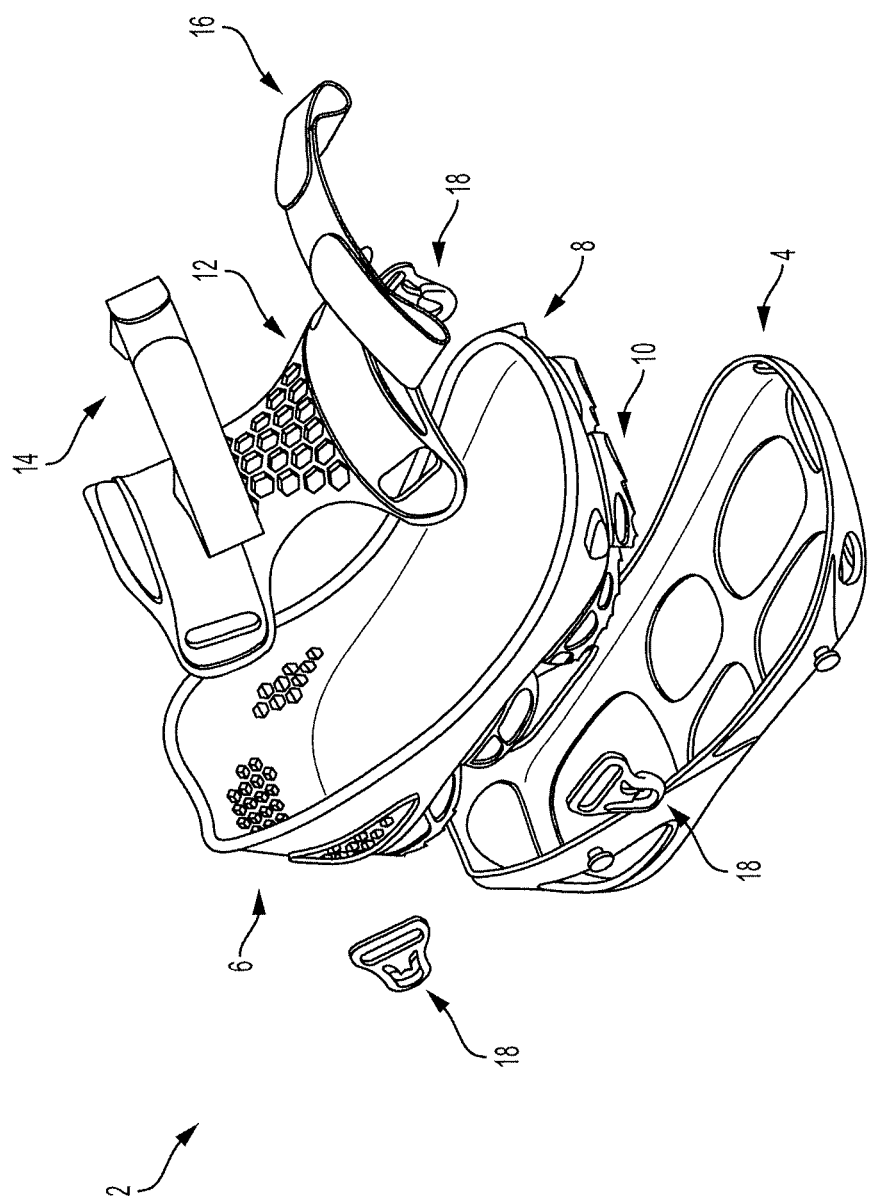
FIG. 2 is an exploded side elevation view of a medical shoe according to an aspect of an exemplary embodiment.

FIG. 1 is a side view of a medical shoe according to an aspect of an exemplary embodiment. FIG. 2 is an exploded side elevation view of a medical shoe according to an aspect of an exemplary embodiment.

A medical shoe 2 according to an aspect of an exemplary embodiment includes a frame 4, a sole assembly 6, and a removable cover 12. The frame 4, sole assembly 6, and removable cover 12 are separable from each other, and are not integrally formed with one another.

The frame 4 is made of a lightweight material and acts as a rigid exoskeleton outside the sole assembly 6. For instance, the frame 4 has a concave interior portion configured to receive the sole assembly 6 so that the sole assembly 6 may be inserted into frame 4. Once sole assembly 6 is inserted into the frame 4, the frame 4 surrounds an exterior circumference of the sole assembly 6, for instance to form a protective barrier around the sole assembly 6.

The sole assembly 6 is an insert for inserting into the frame 4 and includes a midsole portion 8 and an outsole portion 10 (see FIG. 2) that are integrally formed with one another. In other words, the sole assembly 6 may be a single piece comprising the midsole portion 8 and the outsole portion 10. The midsole portion 8 defines a top portion of the sole assembly 6 and includes a foot bed area for contacting and/or supporting a patient's foot. The midsole portion 8 is received into and is surrounded by the frame 4.

The outsole portion 10 defines a bottom portion of the sole assembly 6 and extends from a bottom surface of the midsole portion 8. The outsole portion 10 is made up of a plurality of outsole projections that, in use, form the ground contacting surface of the sole assembly 6.

The frame 4 and the sole assembly 6 are configured to establish a self-locking fit, for instance a snap fit, when the sole assembly 6 is inserted into the frame 4. For instance, as discussed in more detail below, the peripheral shape of the sole assembly 6 may correspond to the peripheral shape of the frame 4 such that the sole assembly 6 is received into the frame 4 and the self-locking fit can be established. Additionally, or in the alternative, projection portions of the outsole portion 10 may be fit into corresponding holes in the frame 4 to reinforce and secure the self-locking fit between the sole assembly 6 and the frame 4. Once the self-locking fit is engaged between the frame 4 and the sole assembly 6 (for instance, as in the configuration shown in FIG. 1), the self-locking fit can be disengaged by separating the sole assembly 6 from the frame 4. This can be done by force, for instance by pulling the frame 4 and the sole assembly 6 in opposite directions.

The frame 4 and the sole assembly 6 may be fully self-locking, such that glue and stitching is not required. In other words, the frame 4 and the sole assembly 6 can be secured without gluing or stitching, and the self-locking fit may be sufficient to secure the frame 4 to the sole assembly 6 for use by a patient. Once the self-locking fit between the frame 4 and the sole assembly 6 is established, a force of friction between the frame 4 and the sole assembly 6 holds the frame 4 and the sole assembly 6 in mutual contact.

As will be discussed later, additional features may be provided to maintain the self-locking fit between the frame 4 and the sole assembly 6. For instance, the sole assembly 6 may include a projection extending from the midsole portion 8 in a substantially horizontal direction. The projection may be received into a corresponding through hole in the frame 4 in order to establish or maintain the self-locking fit between the frame 4 and the sole assembly 6.

As shown in FIG. 2, the removable cover 12 forms a top portion of the medical shoe 2. The removable cover 12 is easily secured to and detached from the frame 4 using a first closure strap 14 and a second closure strap 16. The first closure strap 14 and the second closure strap 16 are able to secure the cover 12 in place in a position above the sole assembly 6.

The first closure strap 14 and the second closure strap 16 may be fastening belts or bands that extend across the face of the removable cover 12, opposite the frame 4 and sole assembly 6, and thus exert a downward force on the removable cover 12 towards the frame 4 and sole assembly 6. The first closure strap 14 and the second closure 16 are oriented on opposite ends of the removable cover 12 (such that the first closure strap 14 is near the patient's ankle and the second closure strap 16 is near the patient's toes, for example). The first closure strap 14 and the second closure strap 16 may be laces for tying, or may include self-engaging hook and loops. The first closure strap 14 and the second closure strap 16 may be fully adjustable, so that the removable cover 12 may be adjusted with respect to the frame 4 and sole assembly 6.

The first closure strap 14 and the second closure strap 16 are secured to the frame 4 by one or more fixation elements 18. The embodiment shown in FIG. 2 shows one fixation element for each strap. That is, fixation element 18 is secured to the frame 4 and receives one of the first closure strap 14 or the second closure strap 16. The structure and attachment of fixation element 18 to the frame 4 is discussed in more detail below.

Once the removable cover 12 is secured to the frame 4, a cavity is defined between the midsole portion 8 of the sole assembly 6 and the removable cover 12 for housing and protecting a foot. As shown in FIG. 1, the cavity includes an ankle opening 20 in a rear area of the medical shoe 2 (i.e. near the patient's ankle), a forefoot opening 22 opposite the ankle opening 20 in a front area of the medical shoe 2 (i.e. near the patient's toes), and a midfoot opening 24 in between the ankle opening 20 and the forefoot opening 22 in a central area of the medical shoe 2. These openings, particularly the forefoot opening 22 and the midfoot opening 24, allow the patient or another person, such as a medical professional, to access the protected foot without removing the medical shoe 2.

The cavity may be configured to receive a foot after the removable cover 12 is secured to the frame 4. In the alternative, the removable cover 12 may be configured to be secured to the frame 4 after a foot has been received into the midsole 8.

Figure 3:
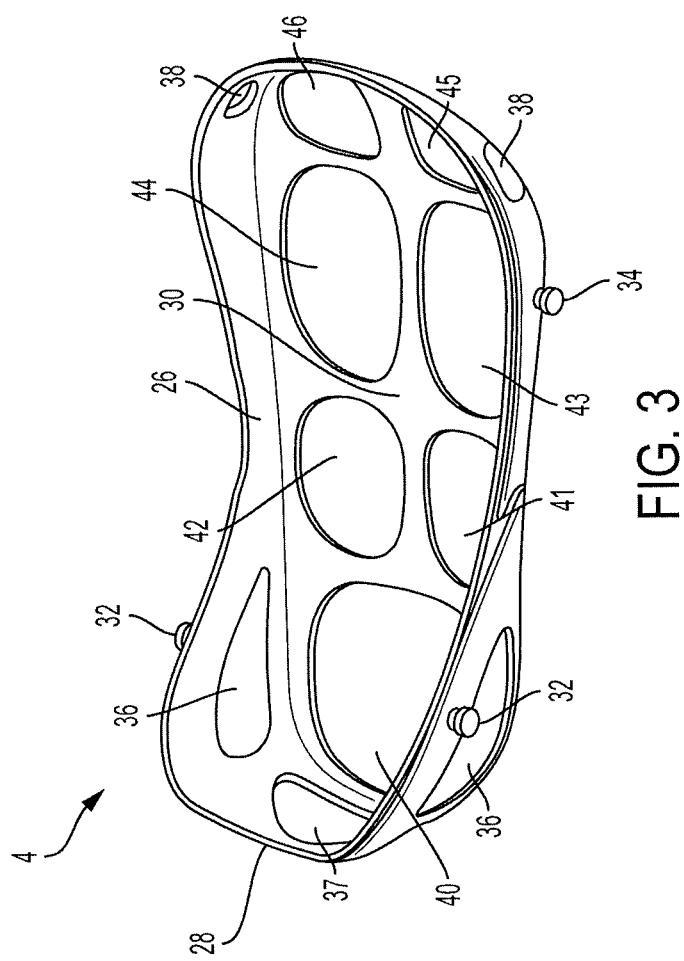
FIG. 3 is a side elevation view of a frame according to an aspect of an exemplary embodiment.

FIG. 3 is a side elevation view of a frame according to an aspect of an exemplary embodiment.

The frame 4 includes a frame lip 26, a frame lip heel portion 28, and a frame web portion 30. The frame web portion 30 is a planar surface of the frame 4 that is parallel or substantially parallel with the midsole portion 8 of the sole assembly 6 when the sole assembly 6 is inserted into the frame 4. The frame lip 26 extends around the edge of the frame web portion 30 in a direction perpendicular to the frame web portion 30, so as to define an outer perimeter of the foot bed and/or to create a wall around the medical shoe 2. For instance, the frame web portion 30 extends in a horizontal plane, while the frame lip 26 extends in a vertical plane around the frame web portion 30.

The frame lip heel portion 28 is an extended portion of the frame lip 26 adjacent to a rear heel area of the midsole portion 8 below the ankle opening 20 of the assembled medical shoe 2. For instance, the frame lip heel portion 28 defines a back wall for supporting the patient's heel and extends further from the frame web portion 30 than the remainder of the frame lip 26. Thus, the frame lip heel portion 28 may provide added support to a rear area of the patient's foot or ankle when the patient's foot is inserted into the medical shoe 2.

The frame lip 26 includes fixation projections 32 and 34 that allow fixation elements 18, for example, of the medical shoe 2 to be secured to the frame 4. The fixation projections 32 and 34 extend from the frame lip 26 in a substantially horizontal direction parallel or substantially parallel with the frame web portion 30. Rear fixation projections 32 are located on both sides of a rear area of the frame lip 26, i.e., on opposing sides of the frame lip heel portion 28. The rear fixation projections 32 are provided on the frame lip heel portion 28 and thus are displaced further from the frame web portion 30 in a vertical direction than front fixation projections 34. Front fixation projections 34 are located on both sides of a front area of the frame lip 26. Thus, fixation projections 32 and 34 are located on opposing sides of the frame 4 at both the rear and front areas, for a total of four fixation projections extending from the frame 4. However, any number of fixation projections may be provided, and the fixation projections 32 and 34 may be located at any position on the frame 4.

The frame lip 26 may include one or more holes 36, 37, and 38 formed therein. As shown in FIG. 3, the frame lip heel portion 28 includes two side ventilation holes 36 and a center ventilation hole 37. The center ventilation hole 37 is centrally located in the frame lip heel portion 28 and corresponds to the rear or back side of the frame 4. The side ventilation holes 36 are symmetrically provided on either side of the center ventilation hole 37.

The frame 4 further includes side projection holes 38 formed in the frame lip 26 that are used to secure other elements to frame 4. As shown in FIG. 3, side projection holes 38 are provided in the frame lip 26 on opposite sides of the front area of the frame 4. However, the side projection holes 38 may be provided at any location of the frame lip 26, including the central area of the frame lip 26 and the rear area of the frame lip 26.

The frame 4 further includes a plurality of through holes 40, 41, 42, 43, 44, 45, and 46 formed in the frame web portion 30. For instance, a heel projection through hole 40 is formed in a rear portion of the frame web portion 30 adjacent to the frame lip heel portion 28. The heel projection through hole 40 may be larger than the other through holes 41, 42, 43, 44, 45, and 46 and is centrally located in the rear area of the frame web portion 30. Midfoot projection through holes 41, 42, 43, and 44 are formed in a central portion of the frame web portion 30 between the rear area and the front area of the frame web portion 30 and may be smaller than the heel projection through hole 40. Midfoot projection though holes 41 and 43 are formed in the frame web portion 30 on a first side of a central axis of the frame web portion 30, and midfoot projection through holes 42 and 44 are formed in the frame web portion 30 on a second side of the central axis of the frame web portion 30. Forefoot projection through holes 45 and 46 are formed in a front area of the frame web portion 30 on each side of the central axis. The projection through holes may be symmetrically oriented such that projection through holes 41, 43, and 45 are mirror images of projection through holes 42, 44, and 46 with respect to the central axis of the web portion 30.

The frame 4 may be made of any light weight rigid material such that the frame 4 provides a form shaping exoskeleton for the medical shoe 2. For instance, the frame 4 may be made of a thermoplastic including polyethylene, polypropylene, polystyrene and polyvinyl chloride. The frame may also be made by a thermoset polymer including polyurethane.

Figure 4A:
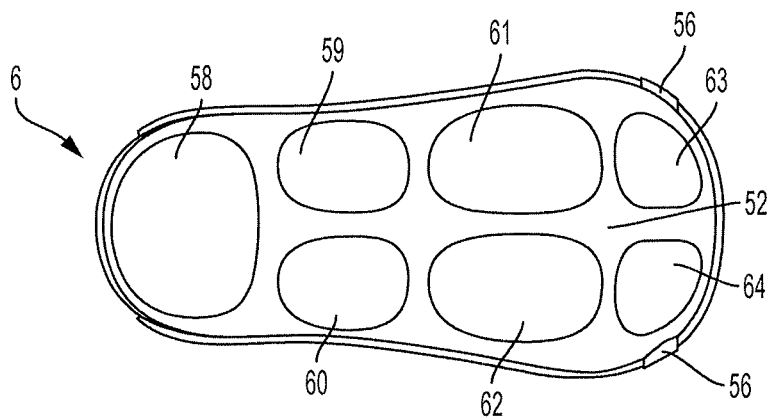
FIGS. 4A, 4B, and 4C are bottom, side, and side elevation views of a sole assembly according to an aspect of an exemplary embodiment.
Figure 4B:
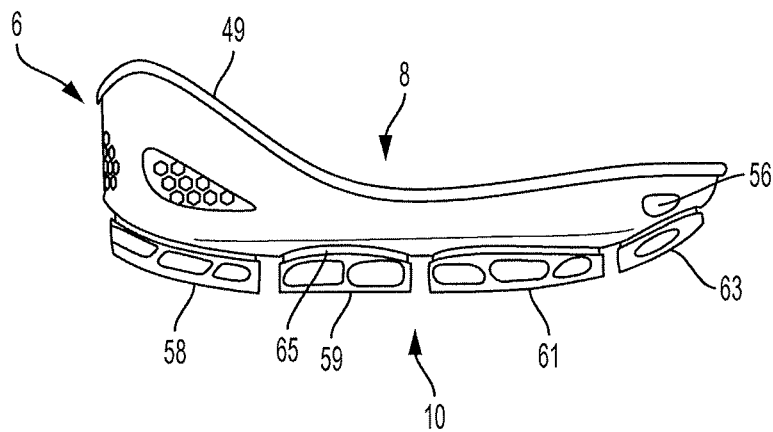
Figure 4C:
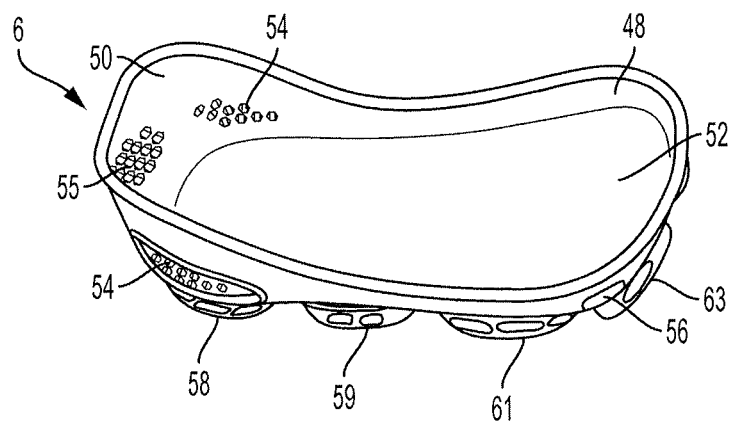

FIGS. 4A, 4B, and 4C are bottom, side, and side elevation views of a sole assembly according to an aspect of an exemplary embodiment.

The sole assembly 6 includes the midsole portion 8 on the top side of the sole assembly 6 and the outsole portion 10 on the bottom of the sole assembly 6. The midsole portion defines the foot bed configured to receive the patient's foot and to be positioned within the frame 4 in the medical shoe 2 once assembled. The outsole portion 10 is configured to form the ground contacting surface of the medical shoe 2 and is configured to extend from the frame 4. The sole assembly 6 defines a rear heel area configured to receive the patient's heel and positioned adjacent to the ankle opening 20 when the medical shoe 2 is assembled. The sole assembly 6 further includes a front forefoot area configured to receive the patients forefoot positioned adjacent to the forefoot opening 22 when the medical shoe 2 is assembled. The sole assembly 6 also includes a midfoot area configured to receive the patient's midfoot positioned adjacent to the midfoot opening 24 when the medical shoe 2 is assembled.

The midsole portion 8 includes a planar foot supporting portion 52 and a midsole lip 48 circumferentially provided around the edge of the foot supporting portion 52. The midsole lip 48 extends in a direction substantially perpendicular to the foot supporting portion 52 so as to create a wall around the edge of the foot supporting portion 52. As shown in FIG. 4C, the midsole lip 48 may create a square forefoot design to act as a bumper to protect the patient's forefoot and to provide a better universal left/right fit.

The midsole lip 48 includes a midsole lip rib 49 and a midsole lip heel portion 50. The midsole lip rib 49 is a rib or raised band extending around the top edge of the midsole lip 48. The midsole lip rib 49 may assist in positioning or seating the sole assembly 6 into the frame 4. For instance, the midsole lip rib 49 may be positioned so as to act as a bumper or stopper and to stop the sole assembly 6 from being inserted farther into the frame 4 once the sole assembly 6 is properly seated in the frame 4. When the sole assembly 6 is inserted into the frame 4, the midsole lip rib may come into contact with the frame lip 28, indicating that the sole assembly 6 is properly seated in the frame 4.

The midsole lip 48 further includes the midsole lip heel portion 50 at the rear area of the midsole portion 8. The midsole lip heel portion 50 extends further away from the foot supporting portion 52 than the remainder of the midsole lip 48, thus defining a heightened back wall for the patient's heel. The midsole lip heel portion 50 may provide additional support to the patient's heel and ankle when the patient's foot is inserted into the sole assembly 6.

The foot supporting portion 52 is generally or substantially planar, and is shaped to receive and support the patient's foot. In other words, although the foot supporting portion 52 is generally flat and extends along a horizontal plane, the foot supporting portion 52 may be curved to correspond to certain contours of the patient's foot. The curvature may include a raised portion in midfoot area of the foot supporting portion 52, for instance to provide additional support to the arches of the patient's foot. The front forefoot area of the foot supporting portion 52 may also include an upward curvature for supporting the patient's forefoot. In the alternative, the foot supporting portion 52 may be flat so as to receive a removable insole.

The midsole lip 48 may include a plurality of ventilation holes 54 and 55 formed in the midsole lip 48 that provide ventilation to the patient's foot. Side ventilation portions 54 are formed on either side of center ventilation portion 55 in the midsole lip heel portion 50 of the midsole lip 48. For instance, when the sole assembly 6 is inserted into the frame 4, the ventilation portions 54 and 55 in the sole assembly 6 are aligned with the ventilation holes 36 and in the frame lip 26. Thus, when assembled, the medical shoe 2 has uninterrupted ventilation holes providing a ventilating current of air to the patient's foot.

Fixation projections 56 are provided on opposing sides on the front area of the midsole lip 48. The fixation projections 56 extend from the midsole lip 48 in a direction substantially perpendicular to the midsole lip 48, i.e., parallel to the foot supporting portion 52. As shown in FIG. 4, two fixation projections 56 are provided in the front area of the midsole portion 8. However, any number of fixation projections 56 may be provided, and they may be positioned at any position along the midsole lip 48.

The outsole portion 10 includes a plurality of projections 58, 59, 60, 61, 62, 63, and 64 extending outwardly from the bottom of the foot supporting portion 52. The projections 58, 59, 60, 61, 62, 63, and 64 may extend in a direction perpendicular or at an angle to the foot supporting portion 52, and the projections may all extend at the same angle or at different angles. A bottom or lower exterior surface of the projections 58, 59, 60, 61, 62, 63, and 64 form the ground contacting surface of the sole assembly 6.

The plurality of projections 58, 59, 60, 61, 62, 63, and 64 include a heel projection 58, four midfoot projections 59, 60,

61, and 62, and two forefoot projections 63 and 64. The heel projection 58 extends from the rear area of the foot support portion 52 adjacent to the midsole lip heel portion 50 and corresponds to the heel of the patient's foot. The heel projection 58 may be larger relative to the remainder of the projections 59, 60, 61, 62, 63, and 64, and is centrally provided on the rear area of the foot supporting portion 52.

The midfoot and forefoot projections 59, 60, 61, 62, 63, and 64 are located on either side of a central axis bisecting the foot supporting portion 52. For instance, projections 59, 61, and 63 are located on a first side of the central axis of the foot supporting portion 52 (i.e., a right side of the patient's foot), while the projections 60, 62, and are located on a second side of the central axis of the foot supporting portion 52 opposite the first side (i.e., a left side of the patient's foot). More so, as shown in FIG. 4A, adjacent projections may be symmetric such that the entire configuration of the outsole portion 10 is symmetric with respect to the central axis. For instance, midfoot projection is symmetric in shape to midfoot projection 60, midfoot projection 61 is symmetric in shape to midfoot projection 62, and forefoot projection 63 is symmetric in shape to forefoot projection 64. Further, heel projection 58 may have a symmetric shape about the central axis. However, the shape and size of the projections may vary, and the possible configurations are not limited to those illustrated herein.

While the heel projection 58 and the midfoot projections 59, 60, 61, and 62 are substantially perpendicular to the foot support portion 52, the forefoot projections 63 and 64 may be provided at an angle to the foot supporting portion 52, as shown in FIG. 4B. For example, the foot supporting portion 52 may be substantially planar, and the forefoot projections 63 and 64 may be provided at an angle to the foot supporting portion 52 so as to point in a forward walking direction. Alternatively, the foot supporting portion 52 may have a curvature, and the forefoot projections 63 and may point in the same forward walking direction while remaining perpendicular to the foot supporting portion 52. By configuring the forefoot projections 63 and 64 at an angle to a walking surface, additional support may be provided to the patient, for instance when walking or stepping.

The symmetry of the outsole portion 10 as shown in FIG. 4A offers significant therapeutic benefits to the medical shoe 2. For example, each of the heel projection 58, the rear midfoot projections 59 and 60, the front midfoot projections 61 and 62, and the forefoot projections 63 and 64 correspond to a particular area of the foot, i.e., the heel, the rear midfoot, the front midfoot, and the forefoot area, respectively. Each of the heel, the rear midfoot, the front midfoot, and the forefoot area of the foot may therefore be isolated and treated individually via the corresponding projections. That is, the projections 58, 59, 60, 61, 62, 63, and 64 may be designed to isolate particular regions of the foot, and may treat each region of the foot depending on a desired offloading scenario. In other words, each of the projections 58, 59, 60, 61, 62, 63, and 64 can be designed and/or modified to address a desired weight distribution across the patient's heel, rear midfoot, front midfoot, and forefoot depending on a condition of the patient's heel, rear midfoot, front midfoot, and forefoot. Two such off-loading scenarios are described in FIGS. 8-9 (discussed below).

Each of the projections 58, 59, 60, 61, 62, 63, and may include an indentation or depression 65 that circumscribes the projection adjacent to the interface with the foot supporting portion 52. The indentation 65 may be continuously formed around the entire circumference of each of the projections, and may assist in securing the sole assembly 6 to the frame 4 by receiving and securing an adjacent portion of the frame web portion 30 into the indentation 65. That is, the frame web portion 30 presses into the indentation 65 around the circumference of each of the projections to secure the frame 4 to the sole assembly 6.

In use, the sole assembly 6 is inserted into the frame 4 such that the sole assembly 6 is received into and seated in the frame 4. Projections 58, 59, 60, 61, 62, 63, and 64 correspond to projection through holes 40, 41, 42, 43, 44, 45, and 46, respectively, and are pushed through to extend from the frame 4 through the projection through holes 40, 41, 42, 43, 44, 45, and 46. In other words, when the sole assembly 6 is properly inserted into the frame 4, the heel projection 58 is pushed through and extends from the heel projection through hole 40, midfoot projections 59, 60, 61, and 62 are pushed through and extend from the midfoot projection through holes 41, 42, 43, and 44, respectively, and the forefoot projections 63 and 64 are pushed through and extend from the forefoot projection through holes 45 and 46, respectively.

When the projections are inserted into and pushed through the respective projection through holes in the frame 4, the sole assembly 6 and the frame 4 are secured to each other by a frictional force, i.e., secured with a snap-fit without gluing or stitching. For example, the midsole lip 48 and the frame lip 26 are configured to have corresponding contours such that when the sole assembly 6 is inserted into the frame 4, a snap fit is established. The contours of the frame lip 26 may mirror the contours of the midsole lip 48 such that the frame lip 26 receives and secures the sole assembly 6 to the frame 4.

The frictional force between the sole assembly 6 and the frame 4 may be aided by various features, for instance the fixation projections 56 extending from the sole assembly 6. When the sole assembly 6 is inserted into the frame 4, the fixation projections 56 are received into the side projection holes 38, ensuring a secure seating of the sole assembly 6 in the frame 4. Also, the ventilation portions 54 and 55 may include ribs circumscribing the ventilation portions 54 and 55 (FIG. 4C) in the sole assembly 6 that may be received into the ventilation holes 36 and 37 to further seat the sole assembly 6 in the frame 4. Finally, the indentations 65 circumscribing the base of each of the projections 58, 59, 60, 61, 62, 63, and 64 may receive an adjacent portion of the frame web portion 30 when the sole assembly 6 is fully inserted into the frame 4. Thus, the indentations 65 are configured to receive and lock the frame 4 in a position where the projections 58, 59, 60, 61, 62, 63, and 64 are fully extended through the projection through holes 40, 41, 42, 43, 44, 45, and 46.

According to an aspect of an exemplary embodiment, the sole assembly 6 may be a patient specific sole assembly. In this case, the sole assembly may be designed according to a specific patient's needs or based off data received from a patient. The data may include foot data, including the size, shape, and/or curvature of the patient's foot. In this case, the midsole portion 8 of the sole assembly 6 may be tailored to the size and curvature of the patient's foot. The foot data may include an image scan, a CT scan, and MRI scan, a mold, or a combination thereof.

The data may also include patient data, i.e., information about a condition of the patient, for instance whether the patient has experienced one or more of surgery of the foot, trauma of the foot, a wound of the foot, or an ulceration of the foot. In this case, the projections may be designed based on the condition of the patient to achieve a therapeutic weight distribution across the patient's foot. The patient data may include data from medical records, data received from a medical database, or data received from a medical professional.

In the alternative, the sole assembly 6 may not be patient specific, and instead may be made without consideration of data from a specific patient. In this case, the midsole portion may be provided in varying sizes, and the patient may be provided with a sole assembly 6 that most closely matches the size of the patient's foot.

The frame 4 may or may not be patient specific depending on the structure of the sole assembly 6. It is contemplated that the frame 4 is designed to be interchangeable with the various configurations of the sole assembly 6. For instance, even if a sole assembly 6 is specially designed to accommodate a larger foot, i.e., by increasing the size of the foot bed, the sole assembly 6 may still be designed to be received into the frame 4 having a standardized size.

The sole assembly 6 may be made of Ethylene-vinyl acetate (EVA), or any other material that is "rubber-like" in softness and flexibility. EVA may also be referred to as expanded rubber or foam rubber. The midsole portion 8 and outsole portion 10 are integrally molded and formed with one mold.

Figure 5A:
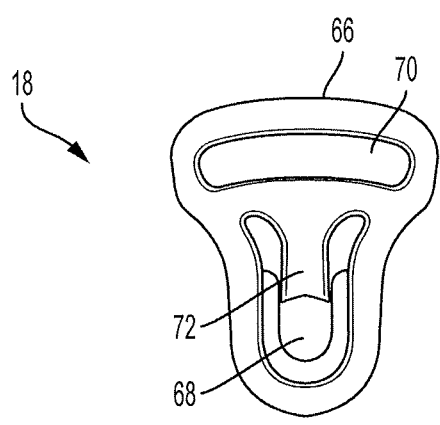
FIGS. 5A and 5B are front and back perspective views of a fixation element according to an aspect of an exemplary embodiment.
Figure 5B:
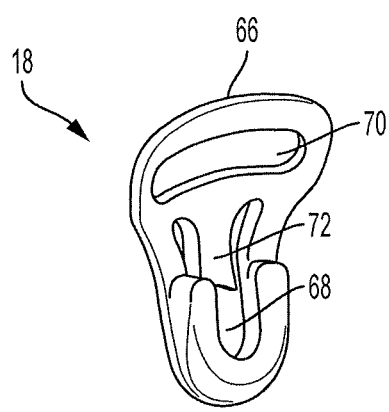

FIGS. 5A and 5B are front and back perspective views of a fixation element according to an aspect of an exemplary embodiment.

The fixation element 18 includes an exterior portion defining an outside edge of the fixation element 18, a projection through hole 68, a closure strap through hole 70, and an interior portion 72. The projection through hole 68 is a hole configured to receive one of the fixation projections 32 and 34 extending from the frame 4. The interior portion 72 is a tooth or projection that borders the projection through hole 68 and defines an edge of the projection through hole 68. The fixation elements 18 are secured to the frame 4 by inserting one of the fixation projections 32 and 34 into the projection through hole 68 of the fixation element 18. The interior portion 72 comes into contact with the fixation projection 32 or 34 and locks the fixation element 18 into place. Either of the first closure strap 14 and the second closure strap 16 may be threaded through the closure strap through hole 70 for securing the cover 12 to the fixation elements 18, and thus to the frame 4. When assembled, a fixation element 18 may be secured to each of the fixation projections 32 and 34 extending from the frame 4.

Figure 6:
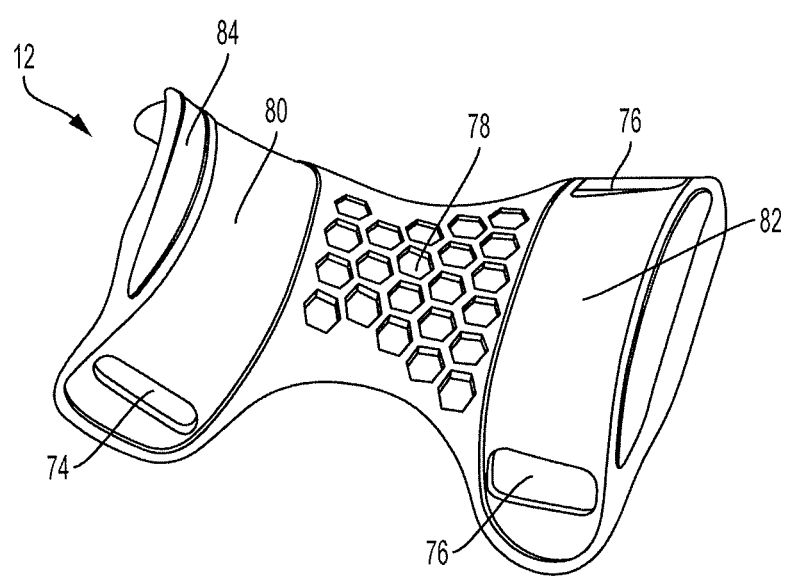
FIG. 6 is a side elevation view of a removable cover according to an aspect of an exemplary embodiment.

FIG. 6 is a side elevation view of a cover according to an aspect of an exemplary embodiment.

Typically, shoes include an upper stitched or otherwise permanently attached to the outsole of the shoe. However, the medical shoe 2 disclosed herein does not require an upper, and instead may have a removable cover 12 that is configured to secure the medical shoe 2 to the patient's foot. The removable cover 12 allows for easy access to the patient's foot, is easily removable and permits easy insertion of the patient's foot into the medical shoe, and eliminates the buckle pressure of traditional shoe securing elements. The cover 12 may be configured to substantially match the contours of the top of the patient's foot, and may include a first closure strap through hole 74 and a second closure strap through hole 76. The cover 12 is secured to the frame 4 via the first closure strap 14, the second closure strap 16, the first closure strap through hole 74, and the second closure strap through hole 76. For instance, the first 14 and second 16 closure straps are threaded through the first 74 and second 76 closure strap through holes, and are secured to a closure strap through hole 70 in a corresponding fixation element 18.

The cover 12 may further include various impressions and indentations in the surface of the cover 12 for added functionality. For instance, the cover 12 further includes a ventilation portion 78 comprising holes formed in the body of the cover 12 in between the first 74 and second 76 closure strap through holes. Thus, when the patient's foot is inserted in the assembled medical shoe 2, the ventilation portion provides ventilating air to the foot of the patient.

The cover 12 may also include depressions formed on the surface of the cover 12 for receiving and positioning the closure straps 14 and 16. For instance, a first closure strap receiving portion 80 and a second closure strap receiving portion 82 for positioning the first 14 and second 16 closure straps are provided on the surface of the cover 12. When the first closure strap 14 is threaded into the first closure strap through hole 74, the first closure strap 14 is received into the first closure strap receiving portion 80 so that the first closure strap 14 does not slide out of position on the face of the cover 12. Similarly, when the second closure strap 16 is threaded into the first closure strap through hole 76, the second closure strap 16 is received into the second closure strap receiving portion 82 so that the second closure strap 16 is secured in place with respect to the cover 12. The cover 12 may also include a cover nameplate 84 for placing advertisements, trademarks, logos, or the like.

In use, the cover 12 is easily separable from the medical shoe 2 using the first 14 and second 16 closure straps. For instance, the first 14 and second 16 closure straps can be unfastened, and the cover 12 can be removed by pulling the cover 12 straight up in a direction away from the sole assembly 6. This removable cover 12 provides multiple advantages, for example, the ability to secure the cover 12 to the frame 4 after the patient's foot has been received into the sole assembly 6. In the alternative, the cover 12 may be secured to the frame 4 prior to the patient's foot being received into the sole assembly 6.

Figure 7:
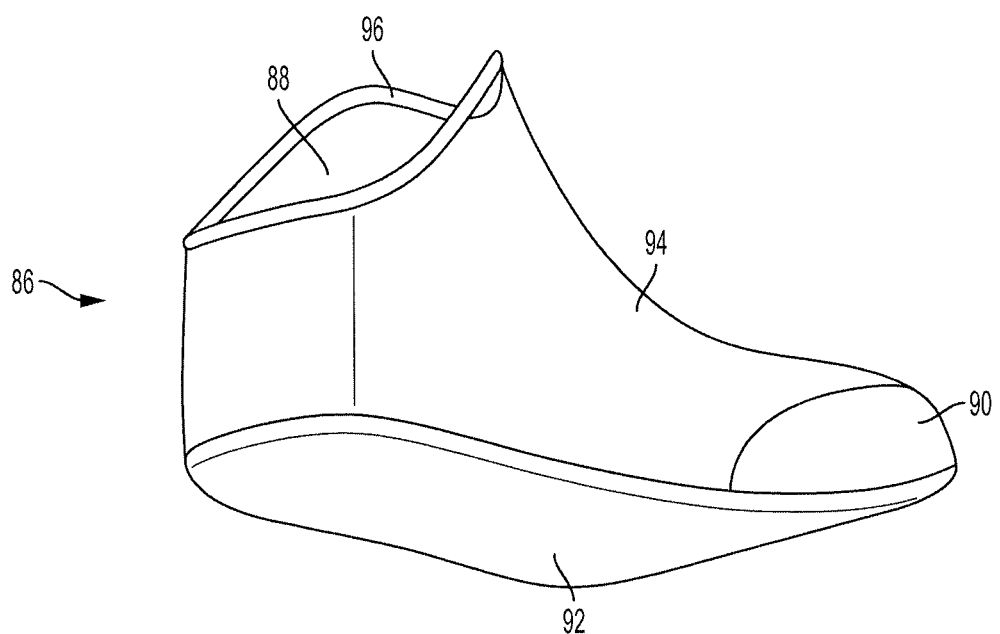
FIG. 7 is a side perspective view of a liner according to an exemplary embodiment.

FIG. 7 is a side perspective view of a liner according to an exemplary embodiment.

A liner 86 may be optionally inserted into the cavity of the medical shoe 2. The liner 86 includes an ankle portion 88, a forefoot portion 90, a foot supporting portion 92, and a body portion 94. The liner 86 may be inserted into the medical shoe 2 such that the forefoot portion 90 corresponds to the forefoot opening 22, the ankle portion 88 corresponds to the ankle opening 20, the body portion 94 corresponds to the midfoot opening 24, and the foot supporting portion 92 corresponds to the foot supporting portion 52. The liner 86 may be inserted into the medical shoe 2 before or after the removable cover 12 is secured to the frame 4 via the first 14 and second 16 closure straps.

The liner 86 may further include an ankle portion rib 96 around a circumference of the ankle portion 88 to ensure proper seating of the liner 86 in the medical shoe 2. For instance, when the liner 86 is inserted into the medical shoe 2, the ankle portion rib 96 may abut an edge of the ankle opening 20 when the liner 86 is properly seated in the medical shoe 2.

Figure 8:
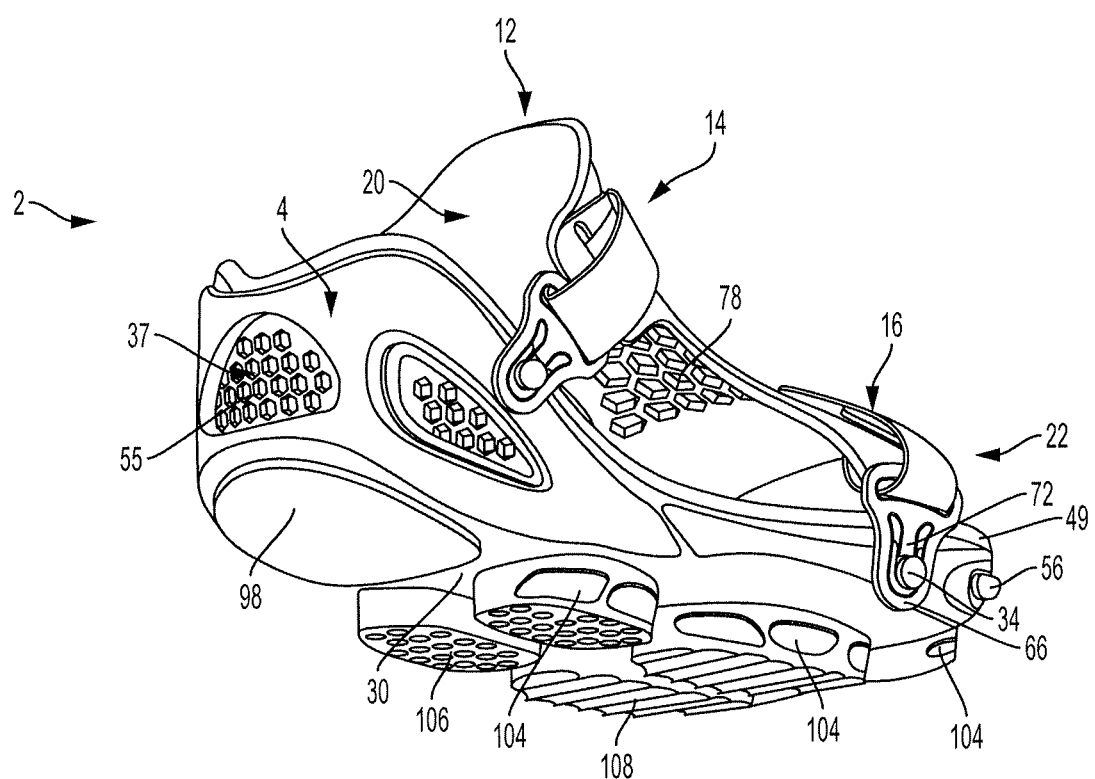
FIG. 8 is a side perspective view of a medical shoe having a modified outsole heel projection according to an aspect of an exemplary embodiment.

FIG. 8 is a side perspective view of a medical shoe having a modified outsole heel projection according to an aspect of an exemplary embodiment.

Depending on the patient's medical condition, it may be desirable to off-load pressure from the patient's heel by shifting weight to the midfoot and forefoot areas, for instance to promote faster healing after surgery, trauma, or when wounds or ulcerations are present on the heel. FIG. 8 is an example of a medical shoe 2 for off-loading weight from the patient's heel and shifting the weight to the midfoot and forefoot areas of the patient's foot. Such an off-loading configuration may be desirable in cases of rear foot trauma, wounds or ulcerations present on the heel area, and post-surgical healing for either soft tissue or bony structure of the heel.

The medical shoe 2 shown in FIG. 8 includes a modified heel projection 98. The modified heel projection 98 is modified to be shorter than the remainder of the outsole projections such that the weight of the patient is off-loaded from the heel area of the patient's foot and is distributed across the remaining projections corresponding to the patient's midfoot and forefoot areas.

One or more of the projections may optionally include side contouring 104, as illustrated in FIG. 8. Also, the ground contacting surface of each of the projections may be either of a low traction ground contact surface 106, or a high traction ground contacting tread 108. The ground contacting tread 108 may have increased traction over the ground contacting surface 106, and thus may be used to create zones of increased traction under each of the projections when increased traction is required.

Figure 9:
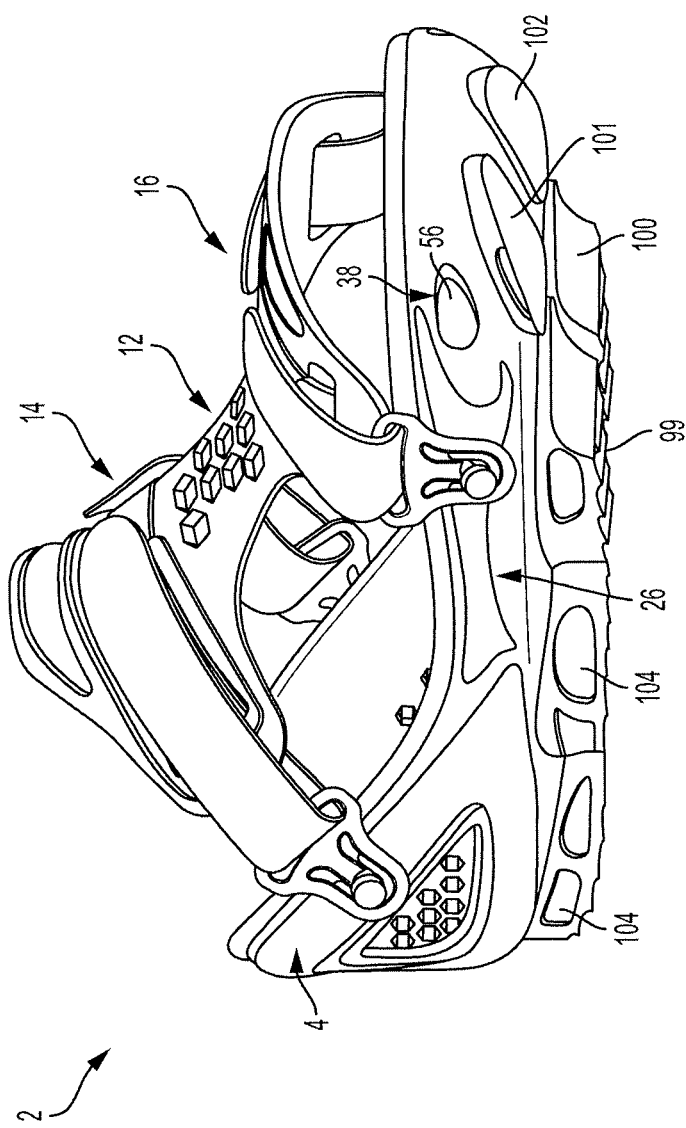
FIG. 9 is a side perspective view of a medical shoe having modified outsole forefoot projections according to an aspect of an exemplary embodiment.

FIG. 9 is a side perspective view of a medical shoe having modified midfoot and forefoot projections according to an aspect of an exemplary embodiment.

In some instances, it may be desirable to reduce weight bearing pressure on the patient's forefoot to promote faster healing after surgery, trauma, or when forefoot wounds or ulcerations are present. Thus, FIG. 9 is an example of a medical shoe 2 for off-loading weight from the patient's forefoot and shifting the weight to the midfoot and heel area.

The medical shoe 2 includes modified forefoot projections 101 and 102 that are shorter than the remaining outsole projections. Midfoot projections 99 and 100 are also modified to include a scalloped or ridged shape, so as to direct weight-bearing pressure away from a front section of the midfoot area.

According to an aspect of an exemplary embodiment, the benefit of the medical shoes of FIGS. 8-9 may be achieved without requiring outsole projections of varying lengths, e.g., wherein each of the outsole projections has the same or a uniform length, as shown in FIG. 1. For example, different offloading scenarios may be achieved by constructing the outsole assembly 6 including the outsole portion 10 of materials having varying densities. By utilizing multi-density materials, for example multi-density EVA foam, area specific pressure reduction can be achieved by strategic placement of low-density materials and high-density materials.

As an example, the benefit of the medical shoe 2 of FIG. 8 can be achieved using a sole assembly 6 including projections 58-64 having the same or a uniform length, as shown in FIG. 1. Rather than providing the modified outsole heel projection 98 of FIG. 8, the outsole heel projection 58 may be constructed of a low-density material, i.e., a material having a lower density than the remaining outsole projections 59-64, such as a relatively lower density EVA foam. With the outsole heel projection 58 being constructed of a lower density material than the remaining outsole projections 59-64, the weight of the patient is off-loaded from the heel area of the patient's foot and is distributed across the remaining projections corresponding to the patient's midfoot and forefoot areas.

Similarly, the benefit of the medical shoe 2 of FIG. 9 can be achieved by constructing the forefoot projections 63 and 64 out of a low-density material, i.e., a material having a lower density than the remaining outsole projections 58-62, such as a relatively lower density EVA foam. With the forefoot projections 63 and 64 being constructed of a lower density material than the remaining outsole projections 58-62, the weight of the patient is off-loaded from the forefoot area of the patient's foot and is distributed across the remaining projections corresponding to the patient's midfoot and heel areas.

According to another aspect of an exemplary embodiments, each of the projections 58-64 may have an independently determined density so as to create a customized off-loading scenario, for example, designed for a specific patient. That is, each of the projections 58-64 may have the same or a different density, and the densities of each of the projections 58-64 may be determined individually so as to create a customized off-loading scenario based on a particular desired off-loading effect. By decreasing the relative density of each projection 58-64, a greater off-loading effect may be achieved with respect to the adjacent portion of the patient's foot.

Figure 10A:
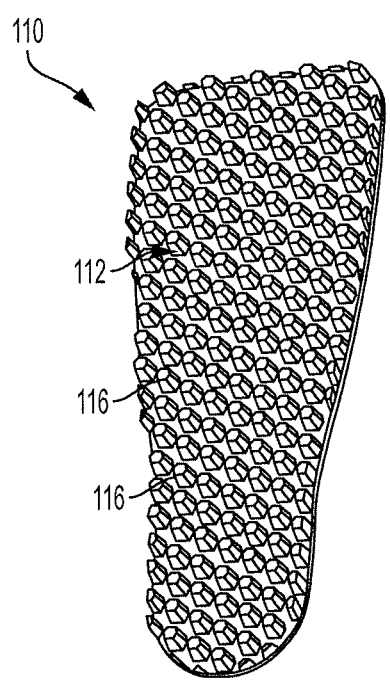
FIGS. 10A and 10B are front and back perspective views of a removable insole according to an aspect of an exemplary embodiment.
Figure 10B:
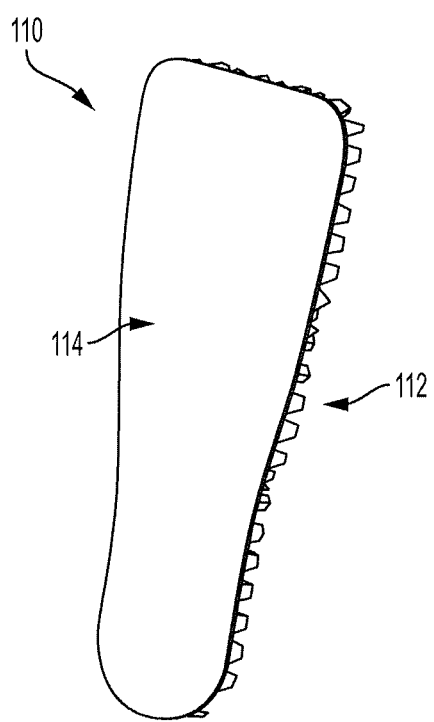

FIGS. 10A and 10B are front and back perspective views of a removable insole according to an aspect of an exemplary embodiment.

The removable insole 110 includes a midsole portion facing side 112 and a foot receiving side 114. The removable insole 110 is configured to be inserted into the medical shoe such that the midsole portion facing side 112 faces the midsole portion 8 of the sole assembly 6, and more specifically the foot supporting portion 52, and such that the foot receiving side 114 faces up towards the cover 12 in order to receive and support the patient's foot.

The removable insole 112 further includes pressure distribution pegs 116 on the midsole portion facing side 112 that provide customizable targeted off-loading of the patient's foot. By adjusting the relative lengths of the pressure distribution pegs 116, weight may be off-loaded from targeted areas of the patient's foot. For instance, pressure distribution pegs 116 adjacent to an injured area of the patient's foot may be made shorter than pressure distribution pegs 116 adjacent to non-injured areas of the patient's foot. Thus, weight can be off-loaded from the injured area of the patient's foot to the non-injured areas of the patient's foot.

Figure 11:
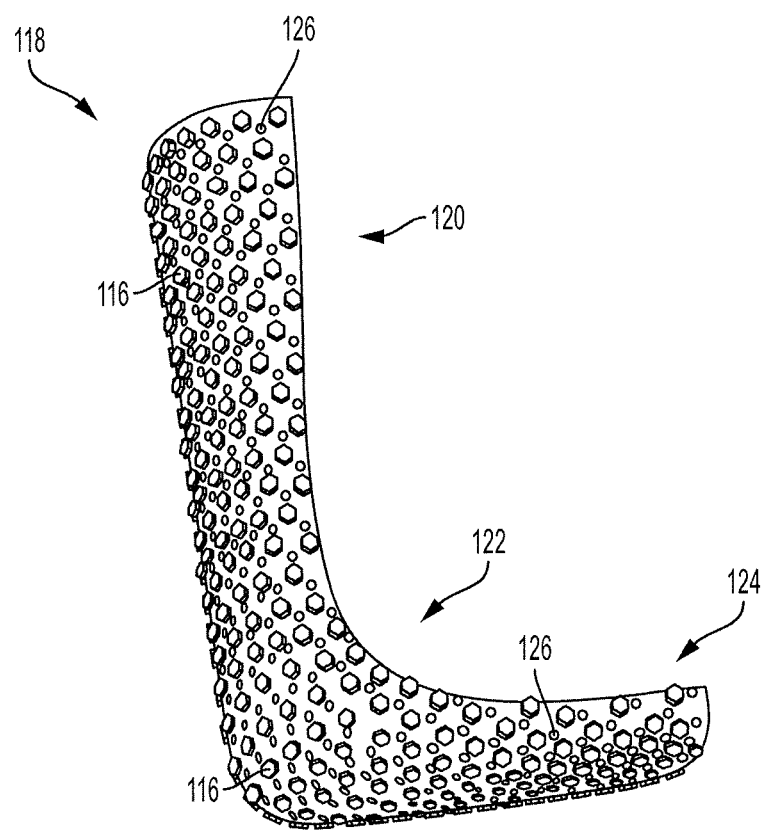
FIG. 11 is a side perspective view of an ankle liner according to an aspect of an exemplary embodiment.

FIG. 11 is a side perspective view of an ankle liner according to an aspect of an exemplary embodiment.

Similar to the removable insole of FIGS. 10A and 10B, an ankle liner 118 may be used for targeted off-loading of the patient's foot and ankle. The ankle liner 118 includes an ankle portion 120, a heel portion 122, and a foot portion 124. The ankle liner 118 is configured to be inserted into the medical shoe 2, and to provide support to the ankle, heel and foot areas of the patient. Thus, the ankle liner 118 extends from the patient's ankle to the patient's forefoot.

The ankle liner 118 also includes the pressure distribution pegs 116 to provide customizable targeted off-loading from patient's ankle, heel, midfoot, and forefoot. By adjusting the relative lengths of the pressure distribution pegs 116, weight may be off-loaded from targeted areas of the patient's ankle and foot.

The ankle liner 118 further includes ventilation holes 126 for providing ventilated air to areas of the patient's ankle and foot. Thus, even when the patient's foot is received into the assembled medical shoe, ventilating air may be provided through the ventilation holes in the ankle liner 118.

Figure 12A:
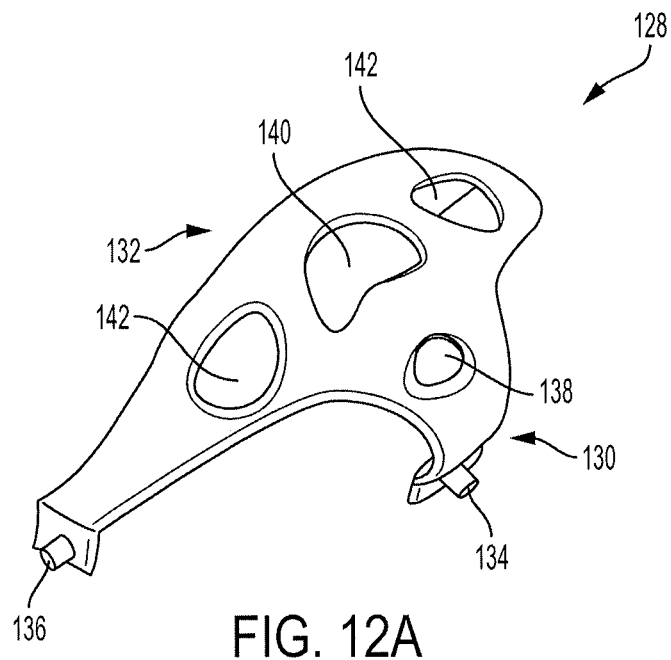
FIGS. 12A and 12B are front and back perspective views of a removable toe cover according to an aspect of an exemplary embodiment.
Figure 12B:
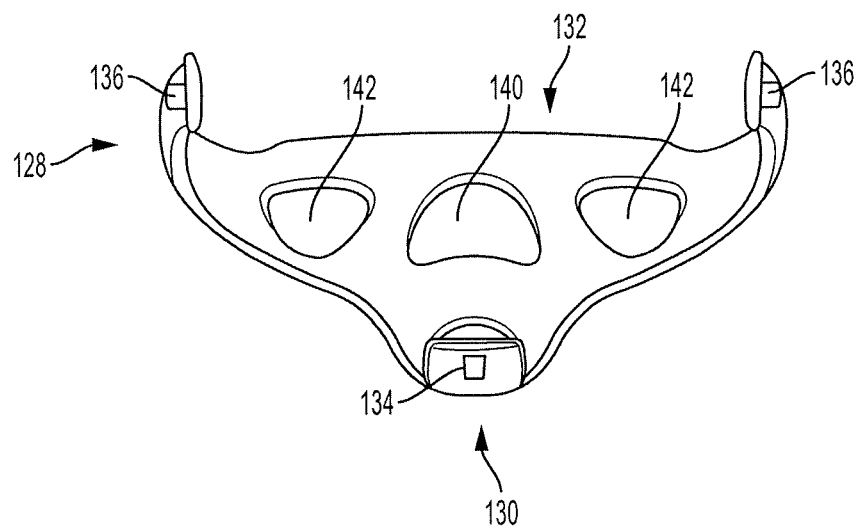
Figure 13:
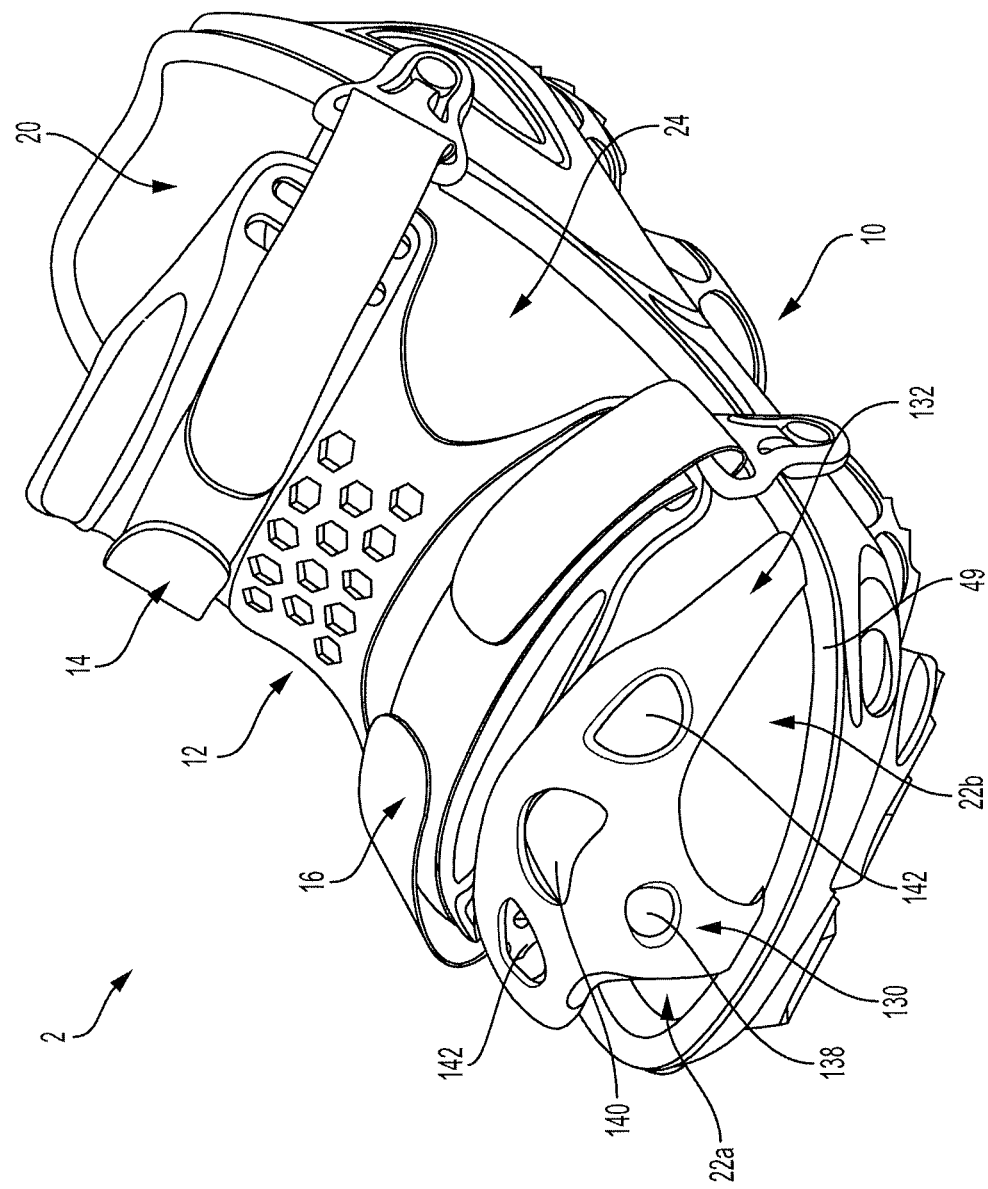
FIG. 13 is a side perspective view of a medical shoe having a removable toe protector according to an aspect of an exemplary embodiment.

FIGS. 12A and 12B are front and back perspective views of a removable toe cover according to an aspect of an exemplary embodiment. FIG. 13 is a side perspective view of a medical shoe having a removable toe protector according to an aspect of an exemplary embodiment.

The medical device 2 may include a detachable toe protector 128 for use when the patient has a wound or other trauma to the toes or front forefoot area. For example, the detachable toe protector 128 may protect the patient's toes and front forefoot area from foreign objects that may agitate or worsen the traumatized region while promoting easy visual inspection thereof.

The toe protector includes two elongated portions, i.e., an anterior portion 130 and a dorsal portion 132. The anterior portion 130 extends from a central area of the dorsal portion 132 in a direction substantially perpendicular to the dorsal portion 132, so as to form a protective guard. The anterior portion 130 and the dorsal portion 132 may also be curved so as to form a cup shape.

The toe protector 128 may include fixation elements 134 and 136 for detachably fixing the toe protector to the medical shoe 2. The fixation elements may include a nub or protrusion extending from a surface of the toe protector 128. However, the exemplary embodiments are not limited thereto, and any fixation element known to provide a detachable connection may be provided, including snaps, magnetic connectors, or the like. An anterior fixation element 134 may be located at an end of the anterior portion 130 opposite the side that the anterior portion 130 is joined to the dorsal portion 132. The dorsal portion 132 may include dorsal fixation elements 136 on both ends thereof.

The toe protector 128 may include holes in the body thereof for promoting easy visual inspection of, as well as for providing a circulating air current to, the patient's toe and front forefoot region. For example, the toe protector 128 may include an anterior hole 138 centrally located in the anterior portion 130. The toe protector 128 may further include a dorsal center hole 140 centrally located in the dorsal portion 132. The dorsal center hole 140 may be surrounded on either side by dorsal side holes 142.

When fixed to the medical shoe 2, as shown in FIG. 13, the toe protector 138 may be received into the sole assembly 6 via the fixation elements 134 and 136 so as to form a protective guard above the forefoot opening 22. For instance, the sole assembly 6 may include a receiving portions (not shown) for receiving the fixation elements 134 and 136 and fixing the toe protector 128 to the sole assembly 6. The receiving portions may include corresponding holes, snaps, or magnetic connectors corresponding to the fixation elements 134 and 136.

The dorsal portion 132 may be positioned across the medical shoe 2 in a direction perpendicular to the patient's foot, i.e., parallel to the first closure strap 14 and the second closure strap 16. The anterior portion 130 may be positioned to extend from the dorsal portion 132 in a direction parallel to the patient's foot, i.e., perpendicular to the first closure strap and the second closure strap. In this configuration, the toe protector 128 substantially fills and protects the patient's foot in the area of the forefoot opening 22. Additionally, the anterior portion 130 bisects the forefoot opening into a first forefoot opening 22a and a second forefoot opening 22b, such that easy visual inspection is maintained.

The toe protector 128 may be made of the same material as the sole assembly 6, for instance, EVA foam, or may be made of a different material suitable for providing protection to the foot. The toe protector 128 is preferably made of a rigid material that is also lightweight and flexible for promoting the patient's comfort, including plastic, polystyrene, expanded polystyrene (EPS), lightweight metals, fiberglass, and the like.

While one or more exemplary embodiments have been described with reference to the figures, it will be understood by those of ordinary skill in the art that various changes in form and details may be made therein without departing from the spirit and scope as defined by the following claims.

What is claimed is:

1. A medical shoe comprising:
   a sole portion configured to support a foot, the sole portion comprising:
      a midsole portion forming a substantially planar surface configured for supporting the foot; and
      an outsole portion comprising a plurality of outsole projections extending from the midsole portion;
   an orthopedic splint comprising a rigid exoskeleton frame surrounding the sole portion, the rigid exoskeleton frame comprising a plurality of through holes corresponding to the plurality of outsole projections; and
   a cover configured to be removably secured to the rigid exoskeleton frame,
   wherein the outsole projections are extended through the through holes in the rigid exoskeleton frame and form a ground contacting surface,
   wherein the sole portion is configured to receive the foot therein both before and after securing the sole portion to the rigid exoskeleton frame, and
   wherein the cover is configured to be secured to the rigid exoskeleton frame after the foot is received in the sole portion secured to the rigid exoskeleton frame.

2. The medical shoe of claim 1, wherein:
   the sole portion further comprises a sole lip portion extending around a circumferential edge of the sole portion in a direction perpendicular to the substantially planar surface,
   the rigid exoskeleton frame further comprises a frame lip portion surrounding the sole portion lip portion such that a contour of an inner surface the frame lip portion corresponds to a contour of an outer surface the sole lip portion,
   the sole lip portion comprises a lip rib that covers an outer surface of the frame lip portion at portions of the frame lip portion furthest away from the substantially planar surface,
   the frame lip portion forms an exoskeleton lip portion, and
   the sole portion is secured to the frame by a self-locking fit that comprises a frictional force between the sole portion and the rigid exoskeleton frame.

3. The medical shoe of claim 2, wherein:
   the sole portion further comprises a fixation projection extending from the sole lip portion in a direction parallel to the substantially planar surface,
   the rigid exoskeleton frame further comprises a fixation projection through hole in the frame lip portion, and
   the fixation projection extends into the fixation projection through hole.

4. The medical shoe of claim 2, wherein:
   the midsole portion comprises a rear heel portion, a midfoot portion, and a front forefoot portion, and
   the plurality of outsole projections comprises:
      a plurality of outsole forefoot projections extending from the front forefoot portion;
      a plurality of outsole midfoot projections extending from the midfoot portion, and
      an outsole heel projection extending from the rear heel portion.

5. The medical shoe of claim 4, wherein a thickness of at least one of the plurality of outsole midfoot projections is greater than a thickness of the outsole heel projection.

6. The medical shoe of claim 4, wherein a thickness of at least one of the plurality of outsole midfoot projections is greater than a thickness of at least one of the plurality of outsole forefoot projections.

7. The medical shoe of claim 4, wherein the sole portion is composed of ethylene-vinyl acetate.

8. The medical shoe of claim 4, wherein the plurality of outsole projections have a non-uniform density.

9. The medical shoe of claim 2, wherein the cover is located above the sole portion, such that a cavity configured to surround the foot is defined by a bottom surface of the removable cover and a top surface of the sole portion.

10. The medical shoe of claim 9, further comprising a fixation element and a closure strap, wherein:
the fixation element is secured to a fixation projection extending from the rigid exoskeleton frame and comprises a fixation element slot configured to receive the closure strap;
the removable cover comprises a removable cover slot configured to receive the closure strap, and
the closure strap is positioned through the fixation element slot and through the removable cover slot.

11. The medical shoe of claim 9, further comprising ventilation holes formed in the removable cover.

12. The medical shoe of claim 1, further comprising a removable insole located on the substantially planar surface, the removable insole comprising:
a foot supporting portion; and
a plurality of pressure distribution pegs extending from the foot supporting portion towards the substantially planar surface,
wherein the plurality of pressure distribution pegs are non-uniform in height.

13. The medical shoe of claim 1,
wherein portions of the outsole projections are extended entirely through the outer openings,
wherein a length of the portions is greater than a length of the through hole in a direction in which the outsole projections are inserted through the outer openings,
wherein the portions comprise side portions adjacent to the ground contacting surface,
wherein the side portions are contoured,
wherein at least a first one of the portions comprises a first tread at the ground contacting surface,
wherein at least a second one of the portions comprises a second tread at the ground contacting surface, and
wherein the first tread comprises a different traction than the second tread.

14. A snap fit medical shoe assembly, comprising
a sole portion configured to support a foot, the sole portion comprising:
a midsole portion forming a substantially planar surface configured for supporting the foot; and
an outsole portion comprising a plurality of outsole projections extending from the midsole portion;
an orthopedic splint comprising a rigid exoskeleton frame configured to surround the sole portion, the rigid exoskeleton frame comprising a plurality of through holes corresponding to the plurality of outsole projections; and
a cover configured to be removably secured to the rigid exoskeleton frame,
wherein the plurality of outsole projections are configured to extend through outer openings of the plurality of through holes in the rigid exoskeleton frame so as to form a ground contacting surface,
wherein the sole portion is configured to receive the foot therein both before and after securing the sole portion to the rigid exoskeleton frame, and
wherein the cover is configured to be secured to the rigid exoskeleton frame after the foot is received in the sole portion secured to the rigid exoskeleton frame.

15. The snap fit medical shoe assembly of claim 14, wherein:
the sole portion further comprises a sole lip portion extending around a circumferential edge of the sole portion in a direction perpendicular to the substantially planar surface,
the rigid exoskeleton frame further comprises an exoskeleton lip portion corresponding to the sole lip portion,
a contour of an inner surface the exoskeleton lip portion corresponds to a contour of an outer surface the sole lip portion, such that the sole portion is configured to be secured to the rigid exoskeleton frame by a snap fit between the sole portion and the rigid exoskeleton frame,
the outer openings face away from the sole portion,
the through holes mirror each other about a central axis of the outsole portion,
the midsole portion comprises a rear heel portion, a midfoot portion, and a front forefoot portion,
the plurality of outsole projections comprises a pair of outsole midfoot projections extending from the midfoot portion, and only one of:
an outsole heel projection extending from the rear heel portion; or
a pair of outsole forefoot projections extending from the front forefoot portion, and
the plurality of outsole projections are provided in a symmetrical pattern.

16. The snap fit medical shoe assembly of claim 15, wherein the plurality of outsole projections comprises the pair of outsole forefoot projections extending from the front forefoot portion, and wherein the pair of outsole forefoot projections are provided at an angle with respect to the substantially planar surface.

17. The snap fit medical shoe assembly of claim 14, wherein the plurality of outsole projections comprises a total of 7 outsole projections.

18. A method of attaching orthopedic bracing, the method comprising:
providing a sole portion configured to support a foot of a patient, the sole portion comprising:
a midsole portion forming a substantially planar surface for supporting the foot; and
an outsole portion comprising a plurality of outsole projections extending from the midsole portion;
providing an orthopedic splint comprising a rigid exoskeleton frame configured to surround the sole portion, the rigid exoskeleton frame comprising a plurality of through holes corresponding to the plurality of outsole projections;
positioning the sole portion into an interior of the rigid exoskeleton frame such that the plurality of outsole projections extend through outer openings of the plurality of through holes in the rigid exoskeleton frame, the plurality of outsole projections forming a ground contacting surface, such that the sole portion is secured to the rigid exoskeleton frame by a snap fit between the sole portion and the rigid exoskeleton; and
removably securing a cover to the rigid exoskeleton frame, and wherein the outer openings face away from the sole portion.

19. The method of claim 18, further comprising:
positioning the substantially planar surface adjacent to a bottom portion of the foot of the patient,
wherein securing the cover to the rigid exoskeleton frame comprises positioning the cover adjacent to a top portion of the foot of the patient,
wherein the plurality of outsole projections are provided in a symmetrical pattern,
wherein the providing the sole portion comprises providing the sole portion based on data of the foot of the patient, such that the plurality of outsole projections are oriented according to a medical condition of the patient,
wherein the sole portion further comprises a sole lip portion extending around a circumferential edge of the sole portion in a direction perpendicular to the substantially planar surface,
wherein the rigid exoskeleton frame further comprises an exoskeleton lip portion corresponding to the sole lip portion,
wherein positioning the sole portion into the interior of the rigid exoskeleton frame is further such that the exoskeleton lip portion of the rigid exoskeleton is positioned such that the sole lip portion is fit into the exoskeleton lip portion, and
wherein the through holes mirror each other about a central axis of the outsole portion.

20. The method of claim 19, wherein the providing the rigid exoskeleton frame comprises providing a rigid exoskeleton frame not based on the data of the foot of the patient.

21. The method of claim 19, wherein the medical condition of the patient is one from among: surgery of the foot, trauma of the foot, a wound of the foot, and an ulceration of the foot.

* * * * *